US012631584B2

(12) United States Patent
Jo et al.

(10) Patent No.: US 12,631,584 B2
(45) Date of Patent: May 19, 2026

(54) CROP CONDITION MONITORING SYSTEM AND CROP CONDITION MONITORING METHOD USING THE SAME

(71) Applicant: National Institute of Meteorological Sciences, Seogwipo-si (KR)

(72) Inventors: Eun Su Jo, Gangneung-si (KR); Kyu Rang Kim, Icheon-si (KR)

(73) Assignee: National Institute of Meteorological Sciences, Seogwipo-si (KR)

( * ) Notice: Subject to any disclaimer, the term of this patent is extended or adjusted under 35 U.S.C. 154(b) by 575 days.

(21) Appl. No.: 18/181,189

(22) Filed: Mar. 9, 2023

(65) Prior Publication Data

US 2023/0288394 A1    Sep. 14, 2023

(30) Foreign Application Priority Data

Mar. 10, 2022    (KR) ........................ 10-2022-0029922
Feb. 7, 2023    (KR) ........................ 10-2023-0015877

(51) Int. Cl.
    *G01N 25/66*        (2006.01)
    *G01N 33/24*        (2006.01)
(52) U.S. Cl.
    CPC ........... *G01N 25/66* (2013.01); *G01N 33/246* (2013.01); *G01N 33/245* (2024.05)
(58) Field of Classification Search
    CPC .... G01N 25/66; G01N 33/246; G01N 33/245; G01N 33/025; G01N 33/24
    See application file for complete search history.

(56) References Cited

U.S. PATENT DOCUMENTS 7,535,237 B1 *   5/2009  Campbell ............ G01N 27/223
                                                        324/696
2005/0212532 A1 *  9/2005  Bernhard ............. G01N 33/246
                                                        324/664

(Continued)

FOREIGN PATENT DOCUMENTS

KR    10-2018-0027778 A    3/2018
KR    10-2021-0025927 A    3/2021

OTHER PUBLICATIONS

Kim Soo-Hyun, et al. "Frost Multi-Observation System—Testing and Operation", Proceedings of the Autumn Meeting of KMS, 2021 (2 page).

(Continued)

*Primary Examiner* — John E Breene
*Assistant Examiner* — Manuel Salvador Castellon, Jr.
(74) *Attorney, Agent, or Firm* — USX IP LLC

(57) ABSTRACT

A crop condition monitoring system includes a first capacitive moisture condition sensor detects a first voltage according to a water condition, a second capacitive moisture condition sensor detects a second voltage according to a water condition, a non-contact surface temperature sensor configured to detect a surface temperature of the first capacitive moisture condition sensor and generate a first surface temperature, a contact surface temperature sensor configured to detect a surface temperature of the second capacitive moisture condition sensor and generate a second surface temperature, the contact surface temperature sensor formed on the second capacitive moisture condition sensor, a temperature and humidity sensor configured to detect a dew point, and a crop condition monitoring server configured to predict the occurrence of dew and frost using the first voltage, the second voltage, the first surface temperature, the (Continued)

second surface temperature, and the dew point received from the temperature and humidity sensor.

4 Claims, 5 Drawing Sheets

(56)                    References Cited

U.S. PATENT DOCUMENTS

2006/0030990 A1 *    2/2006    Anderson ............. G06Q 10/00
                                                                        701/50
2019/0271656 A1 *    9/2019    Pruessner ........... G01N 33/246

OTHER PUBLICATIONS

Supervising Institution: K-Water Co., Ltd., "Development of an Automatic Frost and Dew Observation System", Oct. 30, 2014 (61 pages).
Korean Office Action dated Jun. 15, 2024 in Application No. 10-2023-0015877.
Korean Office Action dated Aug. 9, 2022 in Application No. 10-2022-0029922.
Report of "Development of frost and dew automatic observation system" from TIPA dated Oct. 30, 2014, pp. 1-57.

* cited by examiner

FIG. 5

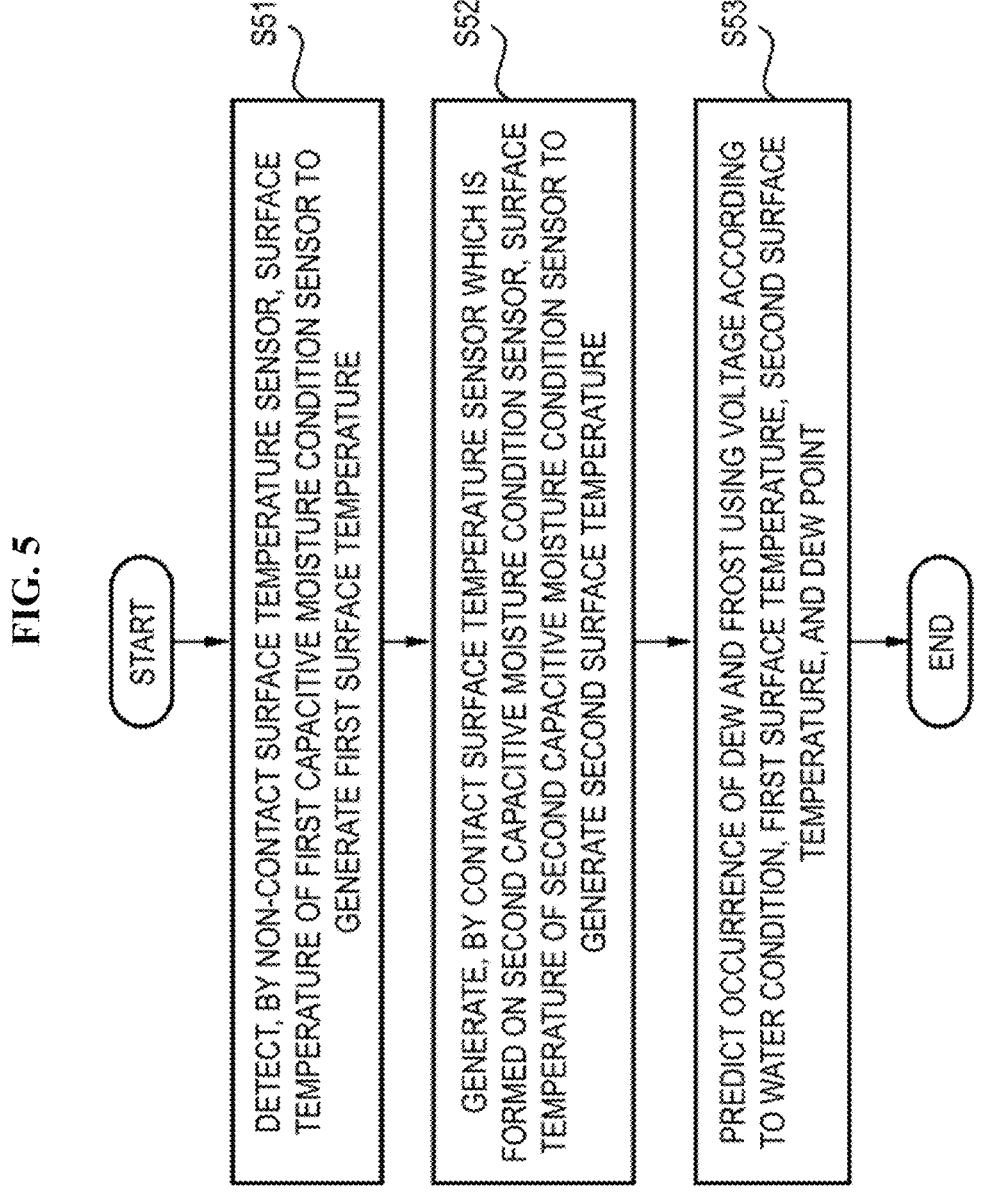

START

S510
DETECT, BY NON-CONTACT SURFACE TEMPERATURE SENSOR, SURFACE TEMPERATURE OF FIRST CAPACITIVE MOISTURE CONDITION SENSOR TO GENERATE FIRST SURFACE TEMPERATURE

S520
GENERATE, BY CONTACT SURFACE TEMPERATURE SENSOR WHICH IS FORMED ON SECOND CAPACITIVE MOISTURE CONDITION SENSOR, SURFACE TEMPERATURE OF SECOND CAPACITIVE MOISTURE CONDITION SENSOR TO GENERATE SECOND SURFACE TEMPERATURE

S530
PREDICT OCCURRENCE OF DEW AND FROST USING VOLTAGE ACCORDING TO WATER CONDITION, FIRST SURFACE TEMPERATURE, SECOND SURFACE TEMPERATURE, AND DEW POINT

END

CROP CONDITION MONITORING SYSTEM AND CROP CONDITION MONITORING METHOD USING THE SAME

CROSS-REFERENCE TO RELATED APPLICATION

This application claims priority to and the benefit of Korean Patent Application No. 10-2022-0029922 and Korean Patent Application No. 10-2023-0015877, filed on Mar. 10, 2022 and Feb. 7, 2023, respectably, the disclosure of which is incorporated herein by reference in its entirety.

BACKGROUND

1. Field of the Invention

The present disclosure relates to a crop condition monitoring system and a crop condition monitoring method using the same, and more particularly, to a crop condition monitoring system that can not only predict the occurrence of dew and frost with high accuracy using a surface temperature and a dew point, but also analyze a change in voltage value according to the condition of water on a surface of a capacitive moisture condition sensor, and a crop condition monitoring method using the same.

2. Discussion of Related Art

In the agricultural sector, dew and frost are major environmental factors for crop production, and it is essential to predict and prepare for the dew and frost. Meteorological data necessary to predict dew and frost occurring on crops includes ① data on the presence or absence of dew and frost, ② data on the surface temperature of crops, and ③ data on the dew point.

However, in current domestic and foreign dew and frost observation systems, by using a capacitive moisture condition sensor, only the presence or absence of dew and frost is observed without the surface temperature and the dew point being observed.

It is commonly known that when the air temperature reaches the dew point, water vapor in the air condenses. However, strictly speaking, the air temperature does not reach the dew point, rather the temperature of a surface of an object in contact with the air should reach the dew point.

Therefore, when data on dew and frost is to be produced using a capacitive moisture condition sensor, a surface temperature of the capacitive moisture condition sensor should also be observed.

However, the capacitive moisture condition sensor only determines and observes the presence or absence of dew and frost and does not observe a surface temperature of a device itself. As a device for observing frost on crops, there are a leaf wetness sensor and a leaf and bud temperature sensor, and each of these devices observes the surface temperature of each device, but does not have a dew and frost determination function.

In order to establish data on dew and frost, not only the phenomena are observed, but also a surface temperature of a subject (i.e., crops, etc.) where the phenomena occur should also be observed. However, there is currently no device or observation system that can observe both of the phenomena and the surface temperature.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

The present disclosure has been made in response to the above-described necessity, the present disclosure is directed to providing a crop condition monitoring system that can not only predict the occurrence of dew and frost with high accuracy using a surface temperature and a dew point, but also analyze a change in voltage value according to the condition of water on a surface of a capacitive moisture condition sensor, and a crop condition monitoring method using the same.

The present disclosure is also directed to providing a crop condition monitoring system that can check a surface temperature more accurately by correcting a surface temperature of a capacitive moisture condition sensor in order to solve a problem that interference may occur due to the attachment of a contact surface temperature sensor formed on the capacitive moisture condition sensor, and a crop condition monitoring method using the same.

The present disclosure is also directed to providing a crop condition monitoring system that can predict the occurrence of dew and frost according to the condition of water on a surface of a capacitive moisture condition sensor according to whether a surface temperature is equal to, above, or below a dew point, and a crop condition monitoring method using the same.

The technical objects of the present disclosure are not limited to those described above, and other technical objects that are not described herein may be clearly understood by those skilled in the art from the following descriptions.

In order to solve the above-described object, a crop condition monitoring system according to an embodiment of the present disclosure includes a first capacitive moisture condition sensor detects a voltage according to a water condition, a second capacitive moisture condition sensor detects a voltage according to a water condition, a non-contact surface temperature sensor configured to detect a surface temperature of the first capacitive moisture condition sensor and generate a first surface temperature, a contact surface temperature sensor configured to detect a surface temperature of the second capacitive moisture condition sensor and generate a second surface temperature, the contact surface temperature sensor formed on the second capacitive moisture condition sensor, a temperature and humidity sensor configured to detect a dew point, and a crop condition monitoring server configured to predict an occurrence of dew and frost using the voltage according to the water condition received from the first capacitive moisture condition sensor, the voltage according to the water condition received from the second capacitive moisture condition sensor, the first surface temperature, the second surface temperature, and the dew point received from the temperature and humidity sensor.

In order to solve the above-described object, a crop condition monitoring method according to an embodiment of the present disclosure includes detecting, by a non-contact surface temperature sensor, a surface temperature of a first capacitive moisture condition sensor and generating a first surface temperature, detecting, by a contact surface temperature sensor formed on a second capacitive moisture condition sensor, a surface temperature of the second capacitive moisture condition sensor and generating a second surface temperature, and predicting, by a crop condition monitoring server, an occurrence of dew and frost using a voltage according to a water condition received from the first capacitive moisture condition sensor, a voltage according to the water condition received from the second capacitive moisture condition sensor, the first surface temperature, the second surface temperature, and a dew point received from a temperature and humidity sensor.

Specific details of other embodiments are included in the detailed description and accompanying drawings.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 5 is a flowchart for describing an example of a crop condition monitoring method according to the present invention.

DETAILED DESCRIPTION

Figure 1:
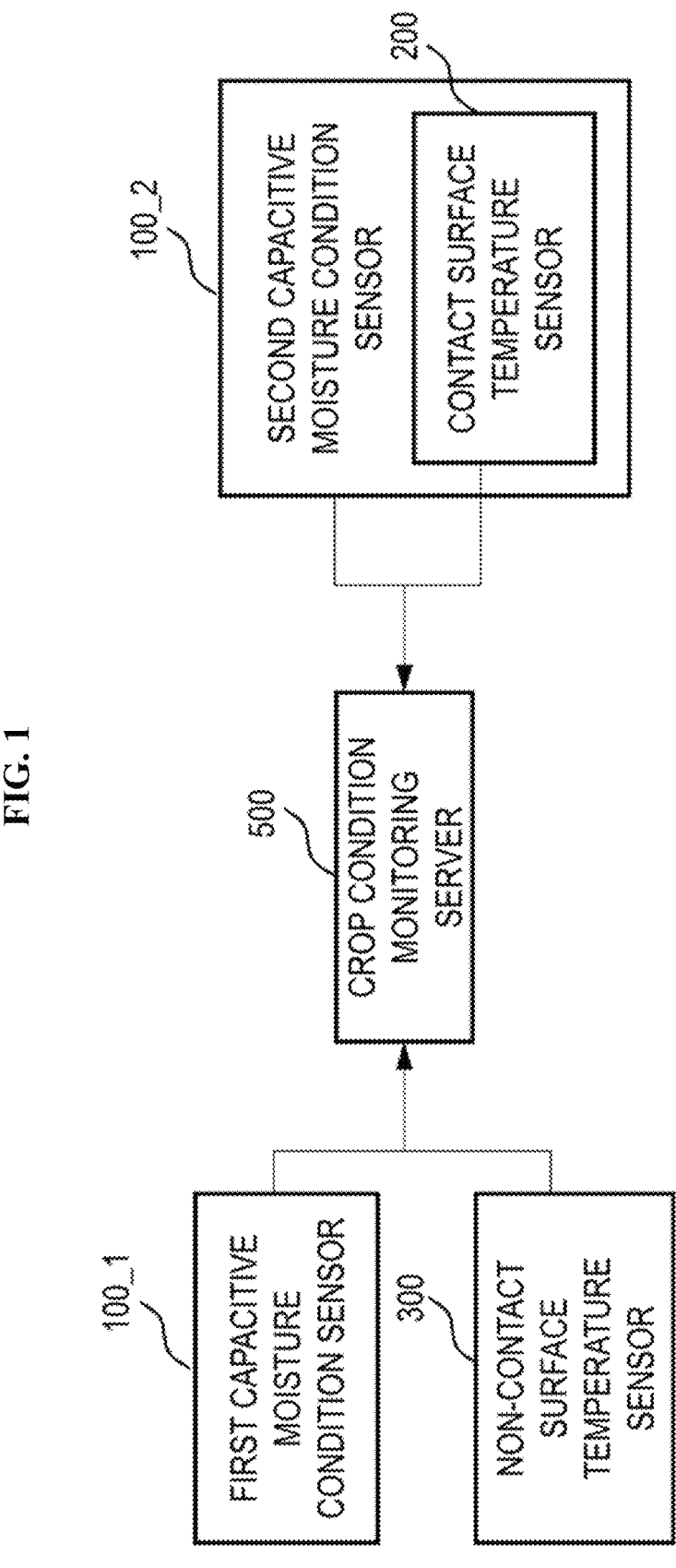
FIG. 1 is a network configuration diagram for describing a crop condition monitoring system according to an embodiment of the present invention.

Advantages and features of the present disclosure and methods of achieving the same will be clearly understood with reference to the accompanying drawings and embodiments described in detail below. However, the present disclosure is not limited to the embodiments to be disclosed below, but may be implemented in various different forms. The embodiments are provided in order to fully explain the present disclosure and fully explain the scope of the present disclosure for those skilled in the art. The scope of the present disclosure is only defined by the appended claims.

In the drawings, like numbers refer to the same or like components, and all combinations described in the specification and claims may be made in any manner. A component referred to in the singular may include one or more components unless otherwise specified, and it should be understood that the singular forms are intended to include the plural forms as well.

The terminology used herein is for the purpose of describing specific exemplary embodiments only and is not intended to limit the present disclosure. As used herein, singular expressions may also be intended to include plural meanings unless the sentence clearly indicates otherwise. The term "and/or" includes any and all combinations of the items listed therewith. It should be further understood that the terms "comprise," "comprising," "include," and/or "including" have an implicit meaning. Accordingly, these terms specify the described features, integers, steps, operations, elements, components, and/or groups thereof but do not preclude the presence or addition of one or more other features, integers, steps, operations, elements, components, and/or groups thereof.

The steps, processes, and operations of the method described herein should not be construed as necessarily performing their performance in such a specific order as discussed or exemplified, unless specifically determined to be an order of performance thereof. It should also be understood that additional or alternative steps may be used.

In addition, each of the components may be implemented as a hardware processor, the above components may be integrated into one hardware processor, or the above components may be combined with each other and implemented as a plurality of hardware processors.

A crop condition monitoring system according to an embodiment of the present disclosure may not only collect data on moisture level and data on a change in condition of water through a capacitive moisture condition sensor that assumes (represents) a subject such as a crop, but also further collect and monitor data on a surface temperature and data on a dew point.

FIG. 1 is a network configuration diagram for describing a crop condition monitoring system according to an embodiment of the present invention.

Referring to FIG. 1, the crop condition monitoring system includes a plurality of capacitive moisture condition sensors 100_1 to 100_2, a contact surface temperature sensor 200, a non-contact surface temperature sensor 300, a temperature and humidity sensor (see 400 in FIG. 3 to be described later), and a crop condition monitoring server 500.

The plurality of capacitive moisture condition sensors 100_1 to 100_2 determine a water condition using a change in voltage.

Among the plurality of capacitive moisture condition sensors 100_1 to 100_2, a first capacitive moisture condition sensor 100_1 determines a water condition using a change in voltage. A surface temperature of the first capacitive moisture condition sensor 100_1 is detected by the non-contact surface temperature sensor 300. Herein after, the surface temperature of the first capacitive moisture condition sensor 100_1 in a moisture condition, which is sensed by the non-contact surface temperature sensor 300, is referred to as a 'first surface temperature'.

The contact surface temperature sensor 200 is formed on a second capacitive moisture condition sensor 100_2 among the plurality of capacitive moisture condition sensors 100_1 to 100_2. Therefore, the contact surface temperature sensor 200 formed on the second capacitive moisture condition sensor 100_2 detects a surface temperature of the second capacitive moisture condition sensor 100_2. Herein after, the surface temperature of the second capacitive moisture condition sensor 100_2 in a moisture condition, which is sensed by the contact surface temperature sensor 200, is referred to as a 'second surface temperature'.

The second capacitive moisture condition sensor 100_2 determines a water condition using a change in voltage. In this case, the water condition may be determined using the change in voltage in consideration of interference caused by the attachment of the contact surface temperature sensor 200 to the second capacitive moisture condition sensor 100_2.

This is because the contact surface temperature sensor 200 formed on the second capacitive moisture condition sensor 100_2 directly detects the surface temperature so that the accuracy is high, but the conduction and radiation characteristics of the contact surface temperature sensor 200 itself may affect the surface temperature of the second capacitive moisture condition sensor 100_2.

As described above, in order to check how much contact surface temperature sensor 200 attached to the second capacitive moisture condition sensor affects the surface temperature of the second capacitive moisture condition sensor, the surface temperature of the first capacitive moisture condition sensor 100_1 among the plurality of capacitive moisture condition sensors 100_1 to 100_2 is detected by the non-contact surface temperature sensor 300. The non-contact surface temperature sensor 300 is an infrared-based sensor and may measure the surface temperature of the first capacitive moisture condition sensor 100_1 through infrared rays.

The temperature and humidity sensor 400 may observe a dew point. The temperature and humidity sensor 400 may calculate a dew point on the basis of measured temperature and relative humidity. As a method of calculating a dew point by the temperature and humidity sensor 400, a conventional method may be used.

The crop condition monitoring server 500 monitors a crop condition using a voltage value according to the water condition received from the first capacitive moisture condition sensor 100_1, a voltage value according to the water condition received from the second capacitive moisture condition sensor 100_2, the first surface temperature of the first capacitive moisture condition sensor 100_1 received from the non-contact surface temperature sensor 300, the second surface temperature of the second capacitive moisture condition sensor 100_2 received from the contact surface temperature sensor 200 formed on the second capacitive moisture condition sensor 100_2, and the dew point received from the temperature and humidity sensor 400.

First, the crop condition monitoring server 500 compares the first surface temperature with the second surface temperature to calculate a difference in surface temperature, and determines whether the difference in surface temperature is greater than or equal to a specific threshold temperature to generate a first determination result.

Thereafter, the crop condition monitoring server 500 compares the voltage value according to the water condition received from the first capacitive moisture condition sensor 100_1 with a voltage value according to a water condition received from the second capacitive moisture condition sensor 100_2 according to the first determination result to generate a second determination result.

In an embodiment, when the first determination result indicates that the difference in surface temperature is greater than or equal to the specific threshold temperature, the crop condition monitoring server 500 compares the voltage value according to the water condition received from the first capacitive moisture condition sensor 100_1 with the voltage value according to the water condition received from the second capacitive moisture condition sensor 100_2 to determine whether the difference in voltage is greater than or equal to the specific threshold voltage and generate the second determination result.

In the above embodiment, when the first determination result indicates that the difference in surface temperature is greater than or equal to the specific threshold temperature and the second determination result indicates that the difference in voltage is greater than or equal to a specific threshold voltage, the crop condition monitoring server 500 reads a correction temperature corresponding to the difference in voltage from a predetermined correction temperature table for each difference in voltage, and corrects the second surface temperature of the second capacitive moisture condition sensor 100_2 using the correction temperature.

That is, since the voltage value according to the water condition detected by the second capacitive moisture condition sensor 100_2 may be interfered with due to the attachment of the contact surface temperature sensor 200, the second surface temperature of the second capacitive moisture condition sensor 100_2 is corrected as much as the correction temperature corresponding to the difference in voltage.

In the above embodiment, when the first determination result indicates that the difference in surface temperature is less than or equal to the specific threshold temperature and the second determination result indicates that the difference in voltage is less than or equal to the specific threshold voltage, the crop condition monitoring server 500 does not correct the second surface temperature of the second capacitive moisture condition sensor 100_2.

That is, when the difference in surface temperature is less than or equal to the specific threshold temperature, the crop condition monitoring server 500 determines that the voltage according to the water condition detected by the second capacitive moisture condition sensor 100_2 is not interfered with due to the attachment of the contact surface temperature sensor 200, and does not correct the second surface temperature of the second capacitive moisture condition sensor 100_2.

In the above embodiment, when the first determination result indicates that the difference in surface temperature is less than or equal to the specific threshold temperature but the second determination result indicates that the difference in voltage is greater than or equal to the specific threshold voltage, the crop condition monitoring server 500 corrects the specific threshold temperature.

That is, when the difference in surface temperature is less than or equal to the specific threshold temperature but the difference in voltage is greater than or equal to the specific threshold voltage, the crop condition monitoring server 500 determines that the specific threshold temperature is set too high, and lowers the specific threshold temperature.

Thereafter, the crop condition monitoring server 500 displays each of the voltage value according to the water condition received from the second capacitive moisture condition sensor 100_2, the surface temperature received from the contact surface temperature sensor 200 formed on the second capacitive moisture condition sensor 100_2, and the dew point received from the temperature and humidity sensor 400 as a graph to monitor the crop condition.

In an embodiment, the crop condition monitoring server 500 may compare the surface temperature and the dew point which are displayed on the graphs, and generate dew occurrence prediction information, frost occurrence prediction information, and precipitation occurrence prediction information according to a result of the comparison.

In the above embodiment, when the surface temperature is less than or equal to the dew point, the crop condition monitoring server 500 may determine that condensation or sublimation is likely to cause frost to generate the frost occurrence prediction information.

In the above embodiment, when the surface temperature is greater than or equal to the dew point, the crop condition monitoring server 500 may determine that dew is likely to be generated to generate the dew occurrence prediction information.

Figure 2:
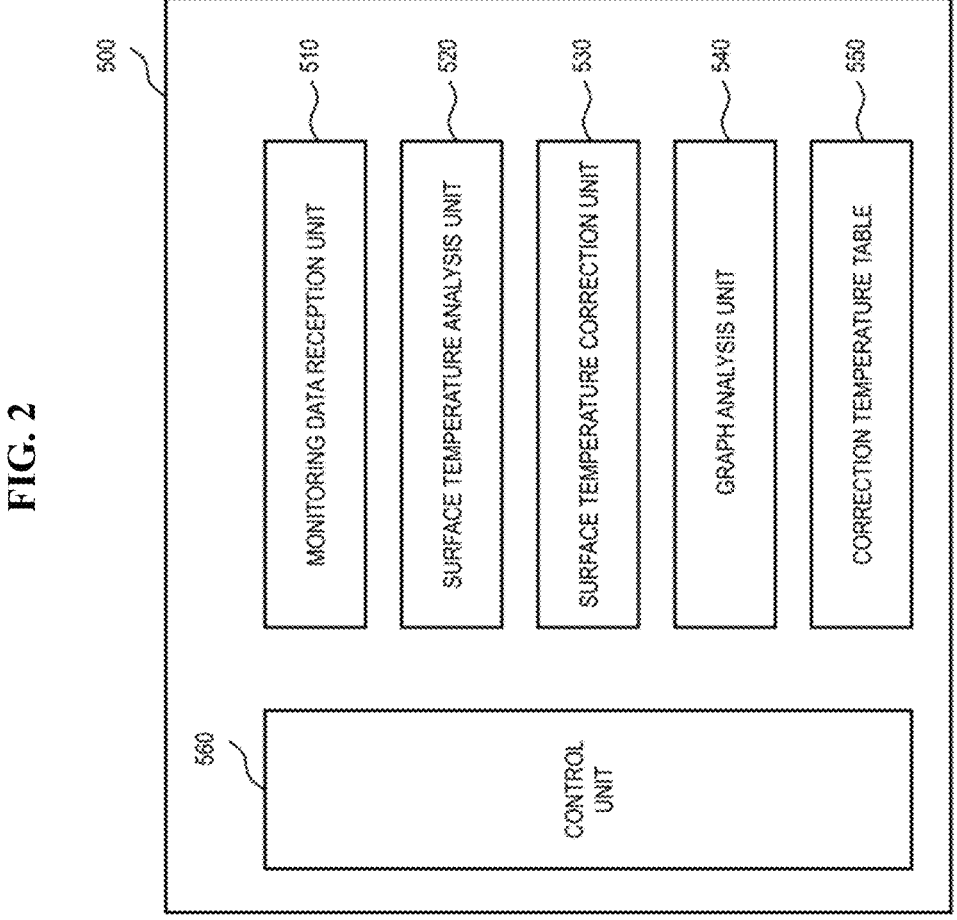
FIG. 2 is a block diagram for describing an internal structure of a crop condition monitoring server according to an embodiment of the present invention.

FIG. 2 is a block diagram for describing an internal structure of a crop condition monitoring server according to an embodiment of the present invention.

Referring to FIG. 2, a crop condition monitoring server 500 includes a monitoring data reception unit 510, a surface temperature analysis unit 520, a surface temperature correction unit 530, a graph analysis unit 540, a correction temperature table 550, and a control unit 560.

The monitoring data reception unit 510 receives a voltage value from a first capacitive moisture condition sensor 100_1, receives a first surface temperature from a non-contact surface temperature sensor 300, receives a second surface temperature from a contact surface temperature sensor 200 formed on a second capacitive moisture condition sensor 100_2, and receives the dew point from a temperature and humidity sensor 400.

The surface temperature analysis unit 520 compares the first surface temperature with the second surface temperature to calculate a difference in surface temperature, and determines whether a difference in surface temperature is greater than or equal to a specific threshold temperature to generate a first determination result.

Thereafter, the surface temperature analysis unit 520 compares a voltage value according to a water condition received from the first capacitive moisture condition sensor 100_1 with a voltage value according to a water condition received from the second capacitive moisture condition sensor 100_2 according to the first determination result to generate a second determination result.

In an embodiment, when the first determination result indicates that the difference in surface temperature is greater than or equal to the specific threshold temperature, the surface temperature analysis unit 520 compares the voltage value according to the water condition received from the first capacitive moisture condition sensor 100_1 with the voltage value according to the water condition received from the second capacitive moisture condition sensor 100_2 to determine whether the difference in voltage is greater than or equal to a specific threshold voltage and generate a second determination result.

In the above embodiment, when the first determination result indicates that the difference in surface temperature is greater than or equal to the specific threshold temperature and the second determination result indicates that the difference in voltage is greater than or equal to the specific threshold voltage, the surface temperature analysis unit 520 reads a correction temperature corresponding to the difference in voltage from a predetermined correction temperature table 550 for each difference in voltage, and provides the correction temperature to the surface temperature correction unit 530 so as to correct the second surface temperature of the second capacitive moisture condition sensor 100_2 using the correction temperature.

That is, since the voltage value according to the water condition detected by the second capacitive moisture condition sensor 100_2 may be interfered with due to the attachment of the contact surface temperature sensor 200, the surface temperature correction unit 530 corrects the second surface temperature of the second capacitive moisture condition sensor 100_2 as much as the correction temperature corresponding to the difference in voltage.

In the above embodiment, when the first determination result indicates that the difference in surface temperature is less than or equal to the specific threshold temperature and the second determination result indicates that the difference in voltage is less than or equal to the specific threshold voltage, the surface temperature analysis unit 520 does not correct the second surface temperature of the second capacitive moisture condition sensor 100_2.

That is, when the difference in surface temperature is less than or equal to the specific threshold temperature, the surface temperature analysis unit 520 determines that the voltage according to the water condition detected by the second capacitive moisture condition sensor 100_2 is not interfered with due to the attachment of the contact surface temperature sensor 200, and does not correct the second surface temperature of the second capacitive moisture condition sensor 100_2.

In the above embodiment, when the first determination result indicates that the difference in surface temperature is less than or equal to the specific threshold temperature but the second determination result indicates that the difference in voltage is greater than or equal to the specific threshold voltage, the surface temperature analysis unit 520 corrects the specific threshold temperature.

That is, when the difference in surface temperature is less than or equal to the specific threshold temperature but the difference in voltage is greater than or equal to the specific threshold voltage, the surface temperature analysis unit 520 determines that the specific threshold temperature is set too high, and lowers the specific threshold temperature.

The graph analysis unit 540 displays each of the voltage value according to the water condition received from the second capacitive moisture condition sensor 100_2, the surface temperature received from the contact surface temperature sensor 200 formed on the second capacitive moisture condition sensor 100_2, and the dew point received from the temperature and humidity sensor 400 as a graph to monitor the crop condition.

In an embodiment, the graph analysis unit 540 may compare the surface temperature and the dew point which are displayed on the graphs, and generate dew occurrence prediction information, frost occurrence prediction information, and precipitation occurrence prediction information according to a result of the comparison.

In the above embodiment, when the surface temperature displayed on the graph is less than or equal to the dew point, the graph analysis unit 540 may determine that condensation or sublimation is likely to cause frost to generate the frost occurrence prediction information.

In the above embodiment, when the surface temperature is greater than or equal to the dew point, the graph analysis unit 540 may determine that dew is likely to be generated to generate the dew occurrence prediction information.

Figure 3:
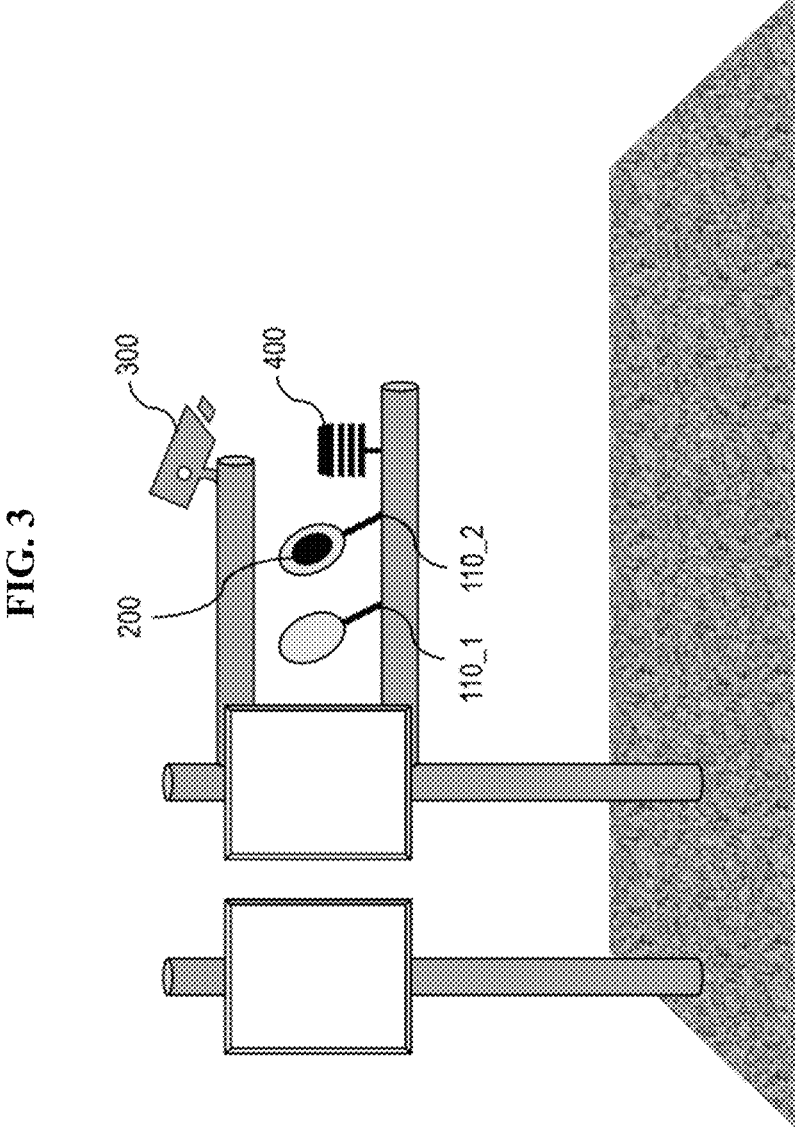
FIG. 3 is an exemplary diagram for describing a crop condition monitoring system according to an embodiment of the present invention.

FIG. 3 is an exemplary diagram for describing a crop condition monitoring system according to an embodiment of the present disclosure.

Referring to FIG. 3, in order to implement the crop condition monitoring system, two rods positioned in the observation field should be installed. In this case, the installed rods should be installed in places where there is no interference of shadows caused by the movement of the sun during the day.

A second capacitive moisture condition sensor 100_2 is a sensor that collects data on moisture level and data on a change in condition of water on a surface of the second capacitive moisture condition sensor 100_2 according to the degree of a change in voltage of the sensor when moisture such as dew forms on a surface of the sensor or when a condition of water changes.

A contact surface temperature sensor 200 that generates a second surface temperature is formed on the second capacitive moisture condition sensor 100_2. Since the contact surface temperature sensor 200 is directly attached to the second capacitive moisture condition sensor 100_2 to observe the surface temperature, the accuracy is high, but the conduction and radiation characteristics of the contact surface temperature sensor 200 itself may affect the surface temperature of the surface temperature of the second capacitive moisture condition sensor 100_2, and thus there is a problem in that it is difficult to accurately measure the surface temperature of the second capacitive moisture condition sensor 100_2.

In order to solve the above problem, in the present disclosure, the non-contact surface temperature sensor 300 that detects a surface temperature of a first capacitive moisture condition sensor 100_1 to generate a first surface temperature is provided. In this case, the non-contact surface temperature sensor 300 is an infrared-based sensor and may measure a surface temperature of the first capacitive moisture condition sensor 100_1, which is a leaf wetness sensor through infrared rays.

A temperature and humidity sensor 400 may observe a dew point. The temperature and humidity sensor 400 may calculate a dew point on the basis of measured temperature and relative humidity. As a method of calculating a dew point by the temperature and humidity sensor 400, a conventional method may be used.

Figure 4:
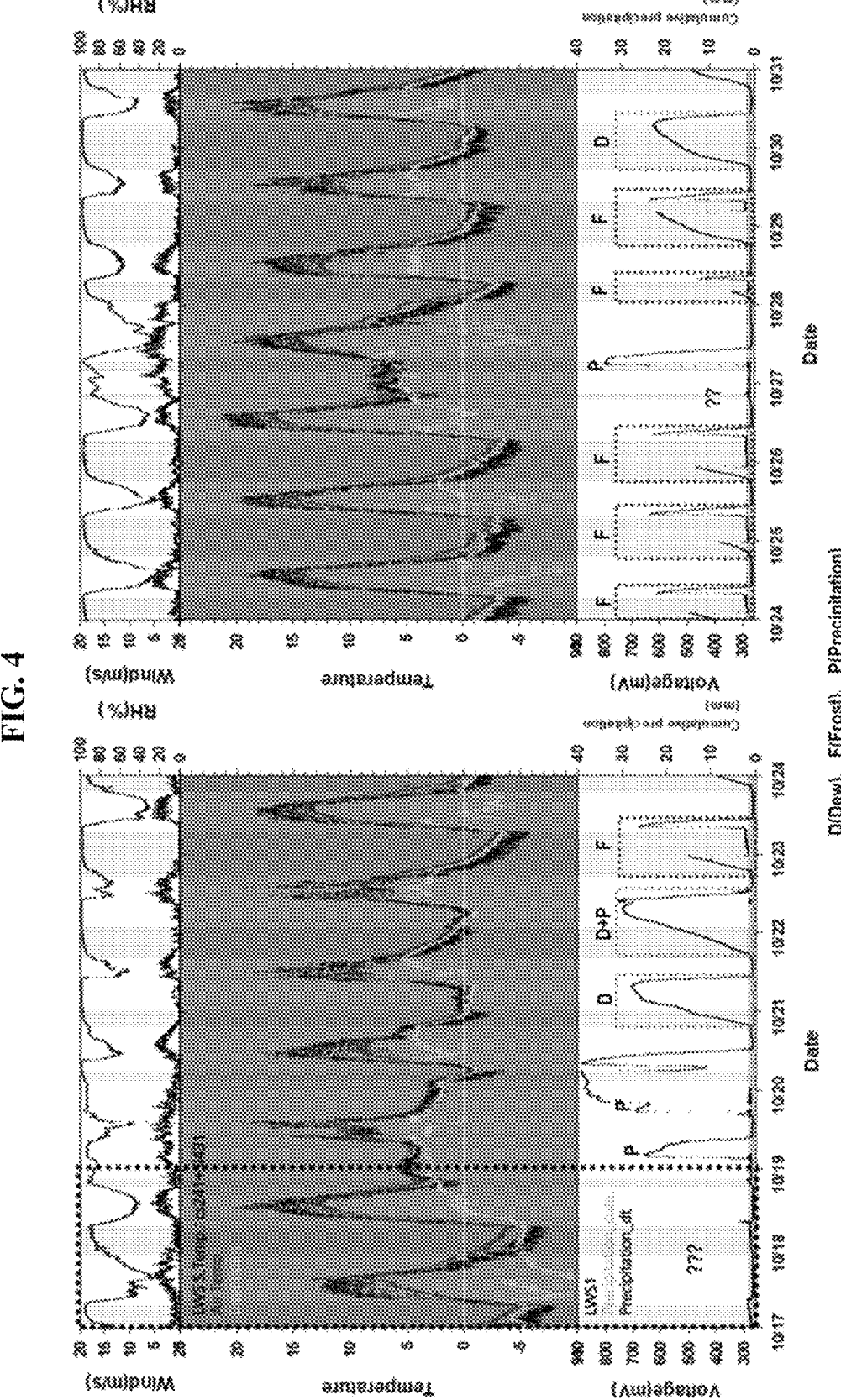
FIG. 4 is a set of graphs for describing a crop condition monitoring process according to the present invention.

FIG. 4 is a set of graphs for describing a crop condition monitoring process according to the present disclosure.

Referring to FIG. 4, a crop condition monitoring server 500 displays each of a voltage value according to a water condition received from a second capacitive moisture condition sensor 100_2, a surface temperature received from a contact surface temperature sensor 200 formed on a second capacitive moisture condition sensor 100_2, and a dew point received from a temperature and humidity sensor 400 as a graph to monitor a crop condition.

Conventionally, only a change in voltage according to a condition of water on a surface of a capacitive moisture condition sensor is observed. However, conventionally, the condition of water cannot be accurately determined only using the change in voltage according to the condition of water on the surface of the capacitive moisture condition sensor, and a surface temperature, which is a major variable for future prediction, cannot be checked.

However, the crop condition monitoring server 500 according to the present disclosure displays each of the voltage value according to the water condition received from the second capacitive moisture condition sensor 100_2, the surface temperature received from the contact surface temperature sensor 200 formed on the second capacitive moisture condition sensor 100_2, and the dew point received from the temperature and humidity sensor 400 as a graph to monitor the crop condition.

In an embodiment, the crop condition monitoring server 500 may compare the surface temperature and the dew point which are displayed on the graphs, and generate dew occurrence prediction information, frost occurrence prediction information, and precipitation occurrence prediction information according to a result of the comparison.

In the above embodiment, when the surface temperature displayed on the graph is less than or equal to the dew point, the crop condition monitoring server 500 may determine that condensation or sublimation is likely to cause frost to generate the frost occurrence prediction information.

In the above embodiment, when the surface temperature is greater than or equal to the dew point, the crop condition monitoring server 500 may determine that dew is likely to be generated to generate the dew occurrence prediction information.

FIG. 5 is a flowchart for describing an example of a crop condition monitoring method according to the present disclosure.

Referring to FIG. 5, a non-contact surface temperature sensor 300 detects a surface temperature of a first capacitive moisture condition sensor 100_1 to generate a first surface temperature (S510).

A contact surface temperature sensor 200 which is formed on a second capacitive moisture condition sensor 100_2 detects a surface temperature of the second capacitive moisture condition sensor 100_2 to generate a second surface temperature (S520).

A crop condition monitoring server 500 predicts the occurrence of dew and frost using a voltage according to the water condition received from the first capacitive moisture condition sensor 100_1, a voltage according to the water condition received from the second capacitive moisture condition sensor 100_2, the first surface temperature, the second surface temperature, and the dew point received from the temperature and humidity sensor 400 (S530).

In an embodiment of operation S530, the crop condition monitoring server 500 displays each of the voltage value according to the water condition received from the second capacitive moisture condition sensor 100_2, the surface temperature received from the contact surface temperature sensor 200 formed on the second capacitive moisture condition sensor 100_2, and the dew point received from the temperature and humidity sensor 400 as a graph to monitor the crop condition.

In an embodiment, the crop condition monitoring server 500 may compare the surface temperature and the dew point which are displayed on the graphs, and generate dew occurrence prediction information, frost occurrence prediction information, and precipitation occurrence prediction information according to a result of the comparison.

In the above embodiment, when the surface temperature displayed on the graph is less than or equal to the dew point, the crop condition monitoring server 500 may determine that condensation or sublimation is likely to cause frost to generate the frost occurrence prediction information.

In the above embodiment, when the surface temperature is greater than or equal to the dew point, the crop condition monitoring server 500 may determine that dew is likely to be generated to generate the dew occurrence prediction information.

As described above, crop condition monitoring system and crop condition monitoring method using the same according to embodiments of the present disclosure have been described. The disclosed embodiments may be implemented in the form of a recording medium configured to store instructions executable by a computer. The instructions may be stored in the form of program code. When the instructions are executed by a processor, the operations of the disclosed embodiments may be performed by a program module being generated thereby. The recording medium may be implemented as a computer-readable recording medium.

The computer-readable recording media include any type of recording media in which computer-decodable instructions are stored. For example, examples of the computer-readable recording media may include a read only memory (ROM), a random-access memory (RAM), a magnetic tape, a magnetic disk, a flash memory, an optical data storage device, and the like.

The computer-readable storage medium may be provided in the form of a non-transitory storage medium. Here, the "non-transitory storage medium" is a tangible device and only means that the storage medium does not include a signal (e.g., electromagnetic wave), and this term does not distinguish that data is semi-permanently or temporarily stored in the storage medium. For example, the "non-transitory storage medium" may include a buffer in which data is temporarily stored.

The methods according to various embodiments disclosed in this specification may be provided by being included in computer program products. The computer program products may be traded between sellers and buyers as commodities. The computer program products may be distributed in the form of a computer-readable storage medium (e.g., compact disc read only memory (CD-ROM)), online (e.g., download or upload) through an application store (e.g., Play Store™), or directly between two user devices (e.g., smartphones). In the case of online distribution, at least some of the computer program products (e.g., downloadable app) may be temporarily stored or temporarily generated in a storage medium such as a memory of a server of a manufacturer, a server of an application store, or a relay server.

According to embodiments of the present disclosure, it is possible to provide a crop condition monitoring system that can not only predict the occurrence of dew and frost with high accuracy by predicting the surface temperature and the dew point as described above, but also analyze a change in voltage value according to the condition of water on a surface of a capacitive moisture condition sensor, and a crop condition monitoring method using the same.

According to embodiments of the present disclosure, it is possible to provide a crop condition monitoring system that can check a surface temperature more accurately by correcting a surface temperature of a capacitive moisture condition sensor in order to solve the problem that interference cause by the contact surface temperature sensor formed on the capacitive moisture condition sensor, and a crop condition monitoring method using the same.

According to embodiments of the present disclosure, it is possible to provide a crop condition monitoring system that can predict the occurrence of dew and frost according to the condition of water on a surface of a capacitive moisture condition sensor according to whether a surface temperature is equal to, above, or below a dew point, and a crop condition monitoring method using the same.

Effects of the present disclosure are not limited to the above-described effects and other effects that are not described may be clearly understood by those skilled in the art from the above detailed descriptions The embodiments of the present disclosure have been described above with reference to the accompanying drawings. It should be understood by those skilled in the art that the present disclosure may be embodied in forms different from the disclosed embodiments without departing from the scope of the present disclosure and without changing essential features thereof. Therefore, the above-described embodiments should be considered in a descriptive sense only and not for purposes of limitation.

What is claimed is:

1. A crop condition monitoring system comprising:
a first capacitive moisture condition sensor configured to detect a first voltage according to a water condition;
a second capacitive moisture condition sensor configured to detect a second voltage according to a water condition;
a non-contact surface temperature sensor configured to detect a surface temperature of the first capacitive moisture condition sensor and generate a first surface temperature of the first capacitive moisture condition senor;
a contact surface temperature sensor formed on the second capacitive moisture condition sensor and configured to detect a surface temperature of the second capacitive moisture condition sensor and generate a second surface temperature of the second capacitive moisture condition sensor;
a temperature and humidity sensor configured to detect a dew point; and
a crop condition monitoring server configured to predict an occurrence of dew and frost based on (i) a difference between the first voltage received from the first capacitive moisture condition sensor and the second voltage received from the second capacitive moisture condition sensor, (ii) a difference between the first surface temperature and the second surface temperature, and (iii) the dew point received from the temperature and humidity sensor.

2. A crop condition monitoring method comprising:
detecting, by a first capacitive moisture condition sensor, a first voltage according to a water condition;
detecting, by a second capacitive moisture condition sensor, a second voltage according to a water condition;
detecting, by a non-contact surface temperature sensor, a surface temperature of the first capacitive moisture condition sensor and generating, by the non-contact surface temperature sensor, a first surface temperature of the first capacitive moisture condition sensor;
detecting, by a contact surface temperature sensor formed on the second capacitive moisture condition sensor, a surface temperature of the second capacitive moisture condition sensor and generating, by the contact surface temperature sensor, a second surface temperature of the second capacitive moisture condition sensor; and
detecting, by a temperature and humidity sensor, a dew point; and
predicting, by a crop condition monitoring server, an occurrence of dew and frost based on (i) a difference between the first voltage received from the first capacitive moisture condition sensor and the second voltage received from the second capacitive moisture condition sensor, (ii) a difference between the first surface temperature and the second surface temperature, and (iii) the dew point received from the temperature and humidity sensor.

3. The crop condition monitoring system of claim 1, wherein the crop condition monitoring server is further configured to, based on the difference between the first surface temperature and the second surface temperature being less than or equal to a specific threshold temperature and the difference between the first voltage and the second voltage being greater than or equal to a specific threshold voltage, correct the specific threshold temperature.

4. The crop condition monitoring method of claim 2, further comprising, based on the difference between the first surface temperature and the second surface temperature being less than or equal to a specific threshold temperature and the difference between the first voltage and the second voltage being greater than or equal to a specific threshold voltage, correcting the specific threshold temperature.

* * * * *